(12) United States Patent
Tanaka et al.

(10) Patent No.: US 6,888,023 B2
(45) Date of Patent: May 3, 2005

(54) PROCESS FOR PRODUCING PYROMELLITIC ACID

(75) Inventors: Kazuo Tanaka, Kurashiki (JP); Hiroshi Ogawa, Kurashiki (JP); Ikutraro Maruki, Kurashiki (JP); Atsushi Okoshi, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/440,255

(22) Filed: May 19, 2003

(65) Prior Publication Data

US 2003/0208091 A1 Nov. 6, 2003

Related U.S. Application Data

(63) Continuation of application No. 10/084,478, filed on Feb. 28, 2002, now abandoned, which is a continuation of application No. 09/560,559, filed on Apr. 28, 2000, now abandoned.

(30) Foreign Application Priority Data

May 10, 1999 (JP) ............................................. 11-128905
Nov. 24, 1999 (JP) ............................................. 11-332850

(51) Int. Cl.$^7$ ............................................. C07C 51/23
(52) U.S. Cl. ..................................................... 562/421
(58) Field of Search ................................. 562/421, 416

(56) References Cited

U.S. PATENT DOCUMENTS

| 3,683,016 A | 8/1972 | Darin et al. |
| 3,920,735 A | 11/1975 | Wampfler et al. |
| 4,824,992 A | 4/1989 | Tanaka et al. |
| 5,895,820 A * | 4/1999 | Tanaka et al. |

FOREIGN PATENT DOCUMENTS

| EP | 0046397 | 2/1982 |
| EP | 0 896 960 A2 | 2/1999 |
| GB | 1 542 231 | 3/1979 |
| JP | 2-184652 | 7/1990 |
| JP | 7-55917 | 6/1995 |
| WO | 98/55441 | 12/1998 |

\* cited by examiner

*Primary Examiner*—Paul A. Zucker
(74) *Attorney, Agent, or Firm*—Wenderoth, Lind & Ponack, L.L.P.

(57) ABSTRACT

A process for producing pyromellitic acid which comprises oxidizing 2,4,5-trimethylbenzaldehyde and/or its oxidized derivative in the presence of a catalyst containing iron, manganese and bromine, or additionally containing zirconium or cerium continuously or semi-continuously using aqueous acetic acid solvent and 0.05–2% by weight of bromide ion. The catalyst used in the present invention has high activity, and the catalyst solution has low corrosive because the reaction is performed at low bromide concentration by using a solvent of aqueous acetic acid. So pyromellitic acid is produced industrially advantageously in high yield continuously or semi-continuously which has been a major difficulty up to now.

8 Claims, No Drawings

PROCESS FOR PRODUCING PYROMELLITIC ACID

This is continuation of Ser. No. 10/084,478, filed Feb. 28, 2002, now abandoned, which is a continuation of Ser. No. 09/560,559, filed Apr. 28, 2000, now abandoned.

FIELD OF THE INVENTION

The present invention relates to process for producing pyromellitic acid which is useful as intermediate for of resin, plasticizers, and for coating. Pyromellitic acid is dehydrated to pyromellitic anhydride and used as a raw material for polyimide resin.

BACKGROUND OF THE INVENTION

Conventionally, aromatic polycarboxylic acids have been produced by oxidation of polyalkylbenzene, trimellitic acid from pseudocumene, trimesic acid from mesitylene, pyromellitic acid from durene and mellophanic acid from iso-durene are known.

In the oxidation of akylbenzenes correspond to aromatic polycarboxylic acids, the alkylbenzenes differ from one another in reactivity depending upon the position of substituted methyl group. Trimellitic acid or pyromellitic acid producd from pseudocumene or durene has a structure in which one carboxylic acid is positioned in opposition to another, resulting in reduced activity of the catalyst activity and a decrease in yield from the oxidation as compared with polymethylbenzenes not having such a structure.

Therefore various proposals have been made for the improvement of the catalyst system. For example, JP-A-Hei-2-184652(1990) discloses a method in which catalyst is charged in two steps in a batch system in the liquid oxidation of durene to pyromellitic acid using Co—Mn—Br catalyst. Although yield of the product is increased by this improvement of the catalyst, this system is complicated and this method is not applicable to continuous or semi continuous-systems because the pyromellitic acid produced decreases the activity of the catalyst.

Polycarboxylic aromatic aldehydes are known as raw materials for producing aromatic polycarboxylic acids. JP-A-Sho-57-38745(1982) discloses a method in which a polycarboxylic aromatic aldehyde is oxidized to produce an aromatic polycarboxylic acid in the presence of cobalt, manganese and bromine in acetic acid solvent. JP-B-Hei-7-116097(1995) discloses a method in which a polycarboxylic aromatic aldehyde is oxidized in the presence of iron, manganese and bromine in water solvent, to produce pyromellic acid.

The catalyst of cobalt, manganese and bromine using polycarboxylic aromatic aldehyde as raw material in JP-Sho-57-38745(1982), results in necessity of the improvement of reaction rate and yield. The problem of corrosion may occur in JP-B-Hei-116097(1995) because the concentration of bromine is high.

SUMMARY OF THE INVENTION

It is an object of the present invention to provide a process for producing pyromellitic acid by oxidizing 2,4,5-trimethylbenzaldehyde and/or its oxidized derivative in which pyromellitic acid is produced advantageously in high yield.

The present inventors assiduously conducted investigations to solve above problems, and have found that Mn—Fe—Zr—Ce—Br catalyst has a higher activity than conventional Co—Mn—Br catalyst in liquid oxidation of 2,4,5-trimethylbenzealdehyde and/or its oxidized derivative and that pyromellitic acid can be produced continuously or semi-continuously using a solvent of aqueous acetic acid.

That is, the present invention provides a process for producing pyromellitic acid, which comprises oxidizing 2,4,5-trimethylbenzaldehyde and/or its oxidized derivative in the presence of a catalyst containing iron, manganese and bromine, or additionally containing zirconium or cerium, continuously or semi-continuously by using aqueous acetic acid solvent.

The first major category of the present invention is continuous oxidation over special ranges of water concentration and reaction temperature. There is provided a process for producing pyromellitic acid which comprises oxidizing 2,4,5-trimethylbenzaldehyde and/or its oxidized derivative in the presence of a catalyst containing iron, manganese and bromine, or additionally containing zirconium and/or cerium, continuously at 180–240° C. using an acetic acid solvent containing 10–90% by weight of water.

The second major category of the present invention is a semi-continuous oxidation over special ranges of Br concentration and through-put (the feed rate of raw material to the liquid weight in a reactor). That is, the present invention provides a process for producing pyromellitic acid which comprises oxidizing 2,4,5-trimethylbenzaldehyde and/or its oxidized derivative semi-continuously using aqueous acetic acid solvent at a through-put of 0.6–1.3 mol/hr-kg in the presence of a catalyst containing iron, manganese and bromine, or additionally containing zirconium or cerium, at a bromine content of 0.05–2% by weight in solvent.

DETAILED DESCRIPTION OF THE INVENTION

As the raw materials for the liquid oxidation of the present invention, 2,4,5-trimethylbenzaldehyde and/or its oxidized derivative are used. As the oxidized derivative, 2,4,5-trimethylbenzoic acid, 1,2-dicarboxy-4,5-phthalide, methyl-trimellitic acid are used.

In the present invention, aqueous acetic acid is used for the solvent of liquid oxidation. The continuous system and semi-continuous system are made possible using this solvent. The water concentration of the solvent is 10–90% by weight, and preferably 20–70% by weight. When the water concentration is lower than this range, recovery and reuse of the catalyst are impossible and reuse of the solvent after the reaction is difficult because manganese salt is mixed with crystals of pyromellitic acid. When the water concentration is lower than this range, the loss of acetic acid by combustion also increases. When the water concentration is higher than this range, the speed of the reaction decreases to lower the yield. In particular the intermediate of the product may remain in the product, resulting in the deterioration of the quality of the product. The more bromine required in order to prevent deterioration, greater the increase in corrosion, and reactors of such high quality material as zirconium are required.

The ratio of the solvent to 2,4,5-trimethylbenzealdehyde and/or its oxidized derivative is 1–25, preferably 3–15 by weight.

The oxidation catalyst used in the present invention is the mixture of manganese compound., bromine compound and iron compound. Zirconium compound and/or cerium compound may be added to these compounds.

As the compounds of manganese, iron, zirconium and cerium, the salts of organic acids, halogens and carbonate may be used. Acetic salt and bromide are particularly preferable.

As the compound of bromine, any compound that generates bromine ion may be used, for example, inorganic bromides such as hydrogen bromide, sodium bromide and manganese bromide, and organic bromide such as tetrabromoethane. Hydrogen bromide and manganese bromide are particularly preferable.

By adding a suitable amount of iron to the Mn—Br catalyst of the present invention, combustion of organic compound is controlled to improve the yield of product greatly and to reduce solvent loss. Addition of zirconium and/or cerium also improves the yield.

The concentration of bromine in solvent is in the range of 0.05–2% by weight, and preferably 0.04–1.8% by weight. When the concentration of bromine is lower than this range, combustion of organic substance increases and the yield decreases. When the concentration of bromine is higher than this range, the reaction become unstable and the yield decreases to suspend the reaction. So it is important to keep the concentration of bromine in this range.

The atomic ratio of bromine to heavy metal is in the range of 0.5–15, and preferably 0.8–8.

The concentration of total heavy metals of manganese, iron, zirconium and cerium in the solvent is 0.03–2% by weight, and preferably 0.05–1% by weight. When the concentration of total heavy metals is too low, the reaction is suspended. When the concentration of total heavy metals is too high, progress of the reaction is hindered. The concentration of iron, zirconium and cerium in the solvent are preferably 1–200 ppm, 1–500 ppm and 1–500 ppm.

The ratio of the each heavy metal to the total heavy metal content is preferably 0–15% by weight in zirconium, 0–15% by weight in cerium, 0.1–15% by weight in iron, and 55–99.9% by weight in manganese.

As the oxygen gas of the present invention, mixtures of oxygen and inert gas such as nitrogen or argon, may be used, and air is used most generally for the liquid oxidation of the present invention. Among various reactors that may be used in the present invention, such as a tank with a stirrer or a bubble tower etc., a tank with a stirrer is preferable as the oxidation reactor because mixing is performed effectively in the tank. The reaction in the present invention is performed continuously or semi-continuously. The temperature of the oxidation is 180–240° C., and preferably 190–230° C. Outside of this range, amount of byproducts is increased and the yield is decreased.

The aforementioned gas containing molecular oxygen is fed continuously into the reactor. The pressure of the gas in the reactor is controlled to 0.5–4 MPa, preferably 1–3 MPa by extracting the reactor gas continuously. The large amount of the solvent and water produced is condensed at the reflux condenser of the reactor. Though most of the solvent and water condensed are refluxed to the reactor, some part of the solvent and water condensed are removed to control the concentration of water in reactor. The concentration of oxygen in off gas from reactor during feed of raw material is 0.1–8% by volume, preferably 1–5% by volume.

The reaction system of the reactor in the first category of the present invention is a continuous type. Plural reactors connected in series are used preferably to increase yield. The hold up time of the reactors in this case is in the range of 0.5–10 hours.

The reaction system of the reactor in the second category of the present invention is a semi-continuous type reactor. In this semi-continuous type, the catalyst solution which catalyst components are dissolved in solvent is fed into the reactor at first. Then blowing a gas containing oxygen into the solution, the mixture of 2,4,5-trimethylbenzealdehyde and/or its oxidized derivative and catalyst solution is fed into the reactor. Reacted solution is not drawn out during oxidation in semi-continuous systems.

Through-put of the reactor, that is feed rate (mol/hr) of raw material to solution (kg) in the reactor is 0.6–1.3 mol/hr-kg, and preferably 0.7–1.1 mol/hr-kg. By controlling the through-put in this range and maintaining the optimum concentration of bromide, the amount of organic substance decomposed is decreased and the yield is increased. When the through-put is lower than 0.6 mol/hr-kg, the amount of organic substance burned is increased. When the through-put is higher than 1.3 mol/hr-kg, the yield is decreased because the reaction is not complete.

After the feed of raw materials and catalyst solution is finished, blowing of oxygen containing gas to the reactor is continued until the oxygen concentration of off-gas from reactor becomes 8% by volume. The total time from the start of catalyst solution feed to the end of blowing out from the reaction is in the range of 0.5–10 hours in semi-continuous system.

The oxidation product mixture after the reaction is cooled to about 10–120° C., preferably about 20–40° C. Then solid products of the oxidation are separated by a filter or a centrifuge. The crude pyromellitic acid separated is rinsed directly or re-slurried using water or aqueous acetic acid to remove organic impurities or metal etc.

Though most of the solution separated above is recycled to the oxidation reactor, some parts of the solution are distillated to remove the water produced, and remainder is re-used as solvent.

According to the first embodiment of the present invention, as will be shown in following example, by oxidizing 2,4,5-trimethylbenzaldehyde and/or its oxidized derivative in the presence of a catalyst containing iron, manganese and bromine, or additionally containing zirconium and/or cerium, and using an acetic acid solvent containing a specific amount of water, pyromellitic acid is produced continuously and in high yield.

According to the second embodiment of the present invention, by oxidizing semi-continuously under optimum conditions of through-put and bromide concentration using the same catalyst, pyromellitic acid is produced in high yield from 2,4,5-trimethylbenzaldehyde and/or its oxidized derivative.

The catalyst used in the present invention has high activity, and the catalyst solution has low corrosion because reaction is performed at low bromine concentrations by using a solvent of aqueous acetic acid. So pyromellitic acid is produced in high yield continuously or semi-continuously which has been a major difficulty up to now.

Preferred Embodiments of the Invention

Some of the preferred embodiments of the present invention will be explained in more detail by referring to Examples and Comparative Examples, which are not intended to limit the scope of the present invention.

PMA used in table showing the result of each Example and Comparative Example and hereafter in the specification means pyromellitic acid. The yield of PMA is the yield of PMA to material 2,4,5-trimethylbenzaldehyde, raw material. The yield of IT means the yield of intermediate of methyltrimellitic acid and 1,2-dicarboxy-4,5-phtalide to 2,4,5-trimethylbenzaldehyde.

Through-put of continuous oxidation is the feed rate of raw material (mol/hr) to weight (kg) of liquid in the reactor.

Through-put of the semi-continuous oxidation is the feed rate of raw material (mol/hr) to average weight (kg) of liquid in the reactor before and after the reaction.

EXAMPLE 1

An autoclave (capacity: 2 liters) made of titanium and equipped with a gas discharge tube having a reflux condenser, a gas introducing tube, a raw material continuous-feed pump and a stirrer was charged with 572 g of a catalyst solution which was prepared by mixing iron(II) bromide, manganese acetate tetrahydrate, 47 wt % hydrogen bromide solution, glacial acetic acid and water, which had an iron content of 0.002% by weight, a manganese content of 0.2% by weight, a bromine content of 1.2% by weight, a water content of 38.6% by weight and a acetic acid content of 60% by weight, then pressurized and heated to 3.0 MPa and 230° C. under a nitrogen atmosphere. The mixture of 133 g/hr of 2,4,5-trimethylbenzaldehyde and 397 g/hr of catalyst solution of the same concentration were charged to the autoclave for 90 minutes. Through-put was 0.7 mol/hr-kg. Air was charged simultaneously with the feed of the mixture of 2,4,5-trimethylbenzaldehyde and catalyst solution, and the reaction was carried out with an off-gas having an oxygen concentration of 4% by volume. Air blowing was continued until oxidation concentration become 15% by volume after the feed of the mixture of 2,4,5-trimethylbenzaldehyde and catalyst solution finished. The oxidation product obtained was analyzed and yield was calculated. Results are shown in Table 4 and Table 5 shows the results.

Comparative Example 1

Example 1 was repeated except that iron(II) bromide was not used in the same reactor. Results are shown in Table 1 and it is confirmed that yield and reaction rate are increased by adding iron.

Comparative Example 2

Example 1 was repeated using cobalt acetate tetrahydrate, which had a manganese content of 0.25% by weight, a cobalt content of 0.10% by weight, a bromine content of 0.4% by weight, a water content of 50% by weight and a acetic acid content of 49% by weight, without using iron(II) bromide in the same reactor. Results are shown in Table 1. It was observed that Fe—Mn—Br catalyst of the present invention provides higher yield and higher reaction rate than Co—Mn—Br catalyst of conventional process.

TABLE 1

|  | Example 1 | Co-Example 1 | Co-Example 2 |
| --- | --- | --- | --- |
| Mn in solvent ppm | 3500 | 3500 | 2500 |
| Co in solvent ppm | 0 | 0 | 1000 |
| Fe in solvent ppm | 8 | 0 | 0 |
| Br in solvent ppm | 4100 | 4100 | 4100 |
| PMA yield mol % | 70.8 | 62.4 | 63.2 |
| IT yield mol % | 6.7 | 11.5 | 8.8 |

EXAMPLES 2–5

Example 1 was repeated using a catalyst containing manganese, iron and zirconium and/or cerium. Zirconium acetate was used as the zirconium compound, and cerium(I) bromide was used as the cerium compound. 1000 g/hr of catalyst solution, 40 g/hr of 2,4,5-trimethylbenzaldehyde and 800 g/hr of catalyst solution were charged to the reactor. Water concentration of the catalyst solution was 50% by weight. Air was charged and the reaction was carried out at 2.5 MPa and 210° C. with an off-gas having an oxygen concentration of 5% by volume. The reaction product was continuously withdrawn so as to maintain a liquid surface at a constant level. Hold-up time of the liquid was about 120 minutes. The oxidation reaction was carried out for 8 hours, and then raw material and catalyst were discharged and air blowing was continued until oxidation concentration of the off gas become 15% by volume. Obtained oxidation product was analyzed and yield was calculated. Results are shown in Table 2.

TABLE 2

|  | Ex-2 | Ex-3 | Ex-4 | Ex-5 |
| --- | --- | --- | --- | --- |
| Mn in solvent ppm | 3600 | 3600 | 3600 | 3600 |
| Fe in solvent ppm | 50 | 50 | 50 | 200 |
| Zr in solvent ppm | 0 | 25 | 25 | 0 |
| Ce in solvent ppm | 0 | 0 | 50 | 0 |
| Br in solvent ppm | 4100 | 4100 | 4100 | 4100 |
| PMA yield mol % | 78.0 | 79.1 | 84.5 | 77.5 |
| IT yield mol % | 1.9 | 1.5 | 1.6 | 2.7 |

The following are confirmed from Table 2.
1. According to the comparison of Example 2 and Example 3, yield is improved by adding a small amount of zirconium to iron.
2. According to the comparison of Example 3 and Example 4, yield is improved by adding small amount of cerium to iron and zirconium.

EXAMPLES 6–7 AND REFERENCE EXAMPLE 1

Example 1 was repeated changing concentration of water in solvent. 1000 g/hr of catalyst solution, 40 g/hr of 2,4,5-trimethylbenzaldehyde and 380 g/hr of catalyst solution were charged to the reactor. Water concentration of the catalyst solution was 50% by weight. Air was charged and the reaction was carried out at 2.5 MPa and 210° C. with an off-gas having an oxygen concentration of 5% by volume. The reaction product was continuously withdrawn so as to maintain a liquid surface at a constant level. Hold-up time of the liquid was about 120 minutes. The oxidation reaction was carried out for 8 hours, and then raw material and catalyst were discharged and air blowing was continued until oxidation concentration of the off gas become 15% by volume. The oxidation product obtained was analyzed and the yield was calculated. The results are shown in Table 3. It was confirmed that yield is decreased by deactivation of the catalyst when water concentration is too low.

TABLE 3

|  | Example 6 | Example 7 | Ref-Example 1 |
| --- | --- | --- | --- |
| Water conc., wt % | 30 | 50 | 5 |
| Co in solvent ppm | 1900 | 1900 | 1900 |
| Fe in solvent ppm | 20 | 20 | 20 |
| Br in solvent ppm | 4500 | 4500 | 4500 |
| PMA yield mol % | 79.0 | 74.0 | 65.0 |
| IT yield mol % | 5.2 | 4.4 | 9.3 |

EXAMPLE 8

Example 7 was repeated using 44 g/hr of 2,4,5-trimethylbenzoic acid instead of 2,4,5-trimethylbenzaldehyde. The yield of PMA was 76.5 mol % and the yield of IT was 3.8 mol %.

EXAMPLE 9

An autoclave (capacity: 2 liters) made of titanium and equipped with a gas discharge tube having a reflux condenser, a gas introducing tube, a raw material continuous-feed pump and a stirrer was charged with 572 g of a catalyst solution which was prepared by mixing iron(II) bromide, manganese acetate tetrahydrate, 47 wt % hydrogen bromide solution, glacial acetic acid and water, which had an iron content of 0.002% by weight, a manganese content of 0.2% by weight, a bromine content of 1.2% by weight, a water content of 38.6% by weight and a acetic acid content of 60% by weight, then pressurized and heated to 3.0 MPa and 230° C. under a nitrogen atmosphere. The mixture of 133 g/hr of 2,4,5-trimethylbenzaldehyde and 397 g/hr of catalyst solution of the same concentration were charged to the autoclave for 90 minutes. Through-put was 0.7 mol/hr-kg. Air was charged simultaneously with the feed of the mixture of 2,4,5-trimethylbenzaldehyde and catalyst solution, and the reaction was carried out with an off-gas having an oxygen concentration of 4% by volume. Air blowing was continued until oxidation concentration become 15% by volume after the feed of the mixture of 2,4,5-trimethylbenzaldehyde and catalyst solution finished. The oxidation product obtained was analyzed and yield was calculated. Results are shown in Table 4 and Table 5 shows the results.

EXAMPLE 10

Continuous reaction was carried out using the same reactor as in Example 9. 1000 g of catalyst solution of the same content as Example 9 was charged at first, then 83 g/hr of 2,4,5-trimethylbenzaldehyde and 690 g/hr of catalyst solution were charged to the reactor. Air was charged and the reaction was carried out at 3.06 MPa and 230° C. with an off-gas having an oxygen concentration of 5% by volume. A reaction product was continuously withdrawn so as to maintain the liquid surface of the reactor at a constant level. Through-put was 0.7 mol/hr-kg. The reaction was carried out for 8 hours, then raw material and catalyst were discharged and air blowing was continued until oxidation concentration of the off gas become 10% by volume. The oxidation product obtained was analyzed and yield was calculated. Results are shown in Table 4. It was confirmed that yield is improved using semi-continuous method.

EXAMPLE 11

Example 9 was repeated feeding in a mixture of 2,4,5-trimethylbenzaldehyde and catalyst solution for 120 minutes. The through-put was 0.5 mol/hr-kg. The results are shown in Table 4. It was confirmed that yield decreases when trough-put was lower than the preferred range.

EXAMPLE 12

Example 9 was repeated feeding in a mixture of 2,4,5-trimethylbenzaldehyde and catalyst solution for 44 minutes. The through-put was 1.4 mol/hr-kg. Results are shown in Table 4. It was confirmed that yield decreases when through-put is higher than preferred range.

TABLE 4

|  | Ex. 9 | Ex. 10 | Ex. 11 | Ex. 12 |
| --- | --- | --- | --- | --- |
| Reaction Type | Semi-con | Cont. | Semi-con | Semi-con |
| Through-put mol/hr-kg | 0.7 | 0.7 | 0.5 | 1.4 |

TABLE 4-continued

|  | Ex. 9 | Ex. 10 | Ex. 11 | Ex. 12 |
| --- | --- | --- | --- | --- |
| PMA yield mol % | 86.1 | 77.2 | 69.1 | 64.9 |
| IT yield mol % | 1.8 | 1.6 | 0.2 | 5.2 |

EXAMPLE 13

Example 9 was repeated using a catalyst solution of 0.6% by weight of bromide. Results are shown in Table 5.

EXAMPLE 14

Example 9 was repeated using a catalyst solution of 1.8% by weight of bromide. Results are shown in Table 5.

Comparative Example 3

Example 9 was repeated using catalyst solution of 0.04% by weight of bromide. Results are shown in Table 5. It was confirmed that pilomellitic acid is not produced when bromide concentration is too low.

TABLE 5

|  | Ex. 9 | Ex. 13 | Ex. 14 | Co-Ex. 3 |
| --- | --- | --- | --- | --- |
| Bromine conc wt % | 1.2 | 0.6 | 1.8 | 0.04 |
| PMA yield mol % | 86.1 | 77.2 | 69.1 | 64.9 |
| IT yield mol % | 1.8 | 1.8 | 0.2 | 5.2 |

EXAMPLE 15

Example 9 was repeated using a catalyst solution which had an iron content of 0.0004% by weight, a manganese content of 0.3% by weight, a bromine content of 0.6%, oxidizing at 2.45 MPa, 210° C. and feeding a mixture of 2,4,5-trimethylbenzaldehyde and catalyst solution for 59 minutes. Through-put was 0.1 mol/hr-kg. The results were shown in Table 6.

EXAMPLE 16

Example 15 was repeated using a catalyst solution which had an iron content of 0.0004% by weight, a manganese content of 0.3% by weight, a bromine content of 0.6% by weight and a zirconium content of 0.005% by weight. The results were shown in Table 6.

TABLE 6

|  | Ex. 15 | Ex. 16 |
| --- | --- | --- |
| Zirconium conc. ppm | 0 | 50 |
| PMA yield mol % | 86.7 | 87.8 |
| IT yield mol % | 4.6 | 4.7 |

What is claimed is:
1. A process for producing pyromellitic acid which comprises oxidizing 2,4,5-trimethylbenzaldehyde and/or its oxidized derivative in the presence of a catalyst containing iron, manganese and bromine, and which may additionally contain zirconium or cerium, continuously or semi-continuously at 180–240° C. by using aqueous acetic acid solvent,
wherein the water concentration of the solvent is 10–90% by weight, the concentration of bromine in the solvent is in the range of 0.05–0.45% by weight and wherein the total concentration of iron, manganese, zirconium and cerium in the solvent is 0.03–2% by weight.

2. The process for producing pyromellitic acid according to claim 1, wherein 2,4,5-trimethylbenzaldehyde and/or its oxidized derivative is oxidized continuously.

3. The process for producing pyromellitic acid according to claim 2, wherein the atomic ratio of bromide ion to the total of the metal is 0.5–15.

4. The process for producing pyromellitic acid according to claim 2, wherein the catalyst has on the basis of total metals, a manganese content of 55–99.9% by weight, an iron content of 0.1–15% by weight, zirconium content of 0–15% by weight and cerium content of 0–15% by weight.

5. The process for producing pyromellitic acid according to claim 2, wherein the iron content is 1–200 ppm, zirconium content is 0–500 ppm and cerium content is 0–500 ppm in the solvent, respectively on the basis of solvent weight.

6. The process for producing pyromellitic acid according to claim 1, wherein 2,4,5-trimethylbenzaldehyde and/or its oxidized derivative is oxidized semi-continuously at a throughput of 0.6–1.3 mol/hr-kg.

7. The process for producing pyromellitic acid according to claim 6, wherein the catalyst has on the basis of total metals, a manganese content of 50–99.9% by weight, an iron content of 0.1–15% by weight, a zirconium content of 0–15% by weight and cerium content of 0–15% by weight.

8. The process for producing pyromellitic acid according to claim 6, wherein the catalyst has, on the basis of total metals, a manganese content of 50–99.99% by weight, an iron content of 1–200 ppm, zirconium content of 0–500 ppm and cerium content of 0–500 ppm in the solvent, respectively on the basis of solvent weight.

* * * * *